United States Patent [19]

Schuftan, deceased

[11] 4,371,381
[45] Feb. 1, 1983

[54] GAS PURIFICATION PROCESS

[75] Inventor: Paul M. Schuftan, deceased, late of Edinburgh, Scotland, by Alice Schuftan, executrix

[73] Assignee: Cryoplants Limited, London, England

[21] Appl. No.: 243,173

[22] Filed: Mar. 12, 1981

[51] Int. Cl.³ ............................................. B01D 53/34
[52] U.S. Cl. ........................................ 55/27; 55/73; 62/24
[58] Field of Search ............... 55/68, 69, 73, 27; 62/24

[56] References Cited
U.S. PATENT DOCUMENTS

| | | | |
|---|---|---|---|
| 3,508,413 | 4/1970 | Paroa | 62/24 |
| 3,702,541 | 11/1972 | Randall et al. | 62/24 X |
| 4,251,247 | 2/1981 | Gauberthier et al. | 62/24 X |
| 4,270,937 | 6/1981 | Adler | 55/68 X |
| 4,274,850 | 6/1981 | Becker | 62/24 |

*Primary Examiner*—John Adee
*Attorney, Agent, or Firm*—David L. Rae; Larry R. Cassett

[57] ABSTRACT

A gas mixture comprising carbon dioxide, at least one gas having a lower boiling point than carbon dioxide, and at least one gaseous impurity having a higher boiling point than carbon dioxide (the impurity typically being hydrogen sulphide) is purified by a rectification process. The gas mixture (typically with a carbon dioxide partial pressure of 20 atmospheres) is precooled to the dewpoint of the carbon dioxide or below and is then rectified to form a liquid fraction relatively rich in the impurity or impurities and a product gaseous fraction relatively lean in or free from the gaseous impurity or impurities. The liquid fraction may be subjected to a second rectification to yield pure carbon dioxide.

10 Claims, 3 Drawing Figures

GAS PURIFICATION PROCESS

BACKGROUND TO THE INVENTION

This invention relates to a gas purification process. It is particularly but not exclusively concerned with removing gaseous impurities of higher boiling point (at 1 atmosphere) than carbon dioxide from a gas mixture containing carbon dioxide, and typically other gases having a lower boiling point than carbon dioxide as well as the impurities. The impurities are typically gaseous compounds of sulphur. The removal of the impurities is accompanied by a significant reduction in the proportion of the carbon dioxide in the gas mixtures.

Gas mixtures which contain such impurities and which are rich in carbon dioxide are, for example, produced by the gasification of carbonaceous materials. Such gas mixtures normally require purification prior to their intended use which may, for example, be for the synthesis of ammonia or methanol; for the production of fuel gas; for hydroforming or liquefaction of hydrogen, or for upgrading hydrocarbon mixtures such as natural gas. In general, complete removal of the impurities is desirable, if not mandatory.

There is also generally a need to remove at least some carbon dioxide from the gas mixture. To avoid pollution of the atmosphere the gaseous impurities separated from the gas mixture will normally have to be rendered innoxious, for example, in the case of compounds of sulphur, by conversion to sulphur. In some processes, a high concentration of sulphur-containing impurities facilitates this conversion and thus selective removal of such impurities from the gas mixture is desirable. As a consequence, some carbon dioxide, practically free from the impurities, will become available as a by-product. It is also desirable that the purification process should keep to a minimum losses of valuable gaseous constituents of relatively low boiling point, for example, methane and hydrogen.

Several commercial processes which substantially meet these requirements are known. For the removal of the impurities and carbon dioxide they all use solvents and absorbents which operate by chemical or physical action. In processes employing solvents, a high circulation rate of the solvent is required. Hence the power consumption and losses of other gaseous constituents by dissolution in the liquid are high. In processes employing chemical absorbents, regeneration of the absorbents at elevated temperatures is required, and fuel costs are high even if heat exchangers are employed. In both kinds of process, solvent or absorbent losses by degradation, vaporisation or leaks can be expensive, and the use of such liquids requires expensive provisions to avoid corrosion of the plant. Finally, currently available means for a selective removal of hydrogen sulphide and carbon dioxide make the purification plant complex, and typically several columns are required for the treatment of the gas mixture with the solvents or absorbents.

Rectification processes for purifying carbon dioxide are known. UK patent specification No. 971 362 relates to a process for removing both more volatile and less volatile impurities from the carbon dioxide. The carbon dioxide is liquefied by heat exchange with 'Freon' (Registered Trade Mark) and then rectified in a first column to remove the more volatile impurities as a gaseous fraction. The liquid fraction is expanded into a second rectification column from which the less volatile impurities are removed as a liquid fraction. French patent specification No. 2 158 338 relates to a process in which the carbon dioxide is liquefied by heat exchange with a refrigerant, the liquid is rectified in a first rectification column to remove the more volatile impurities and then rectified in a second column operating at a higher pressure than the first to remove the less volatile impurities. U.S. Pat. No. 4,152,129 relates to a process in which only more volatile constituents are removed from the carbon dioxide by rectification.

OBJECTS OF THE INVENTION

It is an object of the invention to remove gaseous impurities of higher boiling point than carbon dioxide from a gas mixture comprising carbon dioxide and at least one gas having a lower boiling point than carbon dioxide by a low temperature rectification method.

It is another object of the invention to provide a rectification method for purifying a gas mixture comprising carbon dioxide, at least one gas having a lower boiling point than carbon dioxide and at least one gaseous impurity having a higher boiling point, wherein substantially no external refrigeration source is required if the incoming gas mixture contains its carbon dioxide at a higher partial pressure.

It is a further object of the invention to provide a method for removing the gaseous impurity of higher boiling point than carbon dioxide from a gas mixture containing carbon dioxide and at least one gas of lower boiling point than carbon dioxide and to produce a product gaseous fraction having a lower concentration of carbon dioxide than the incoming gas mixture.

It is yet a further object of the invention to provide a method for purifying a gas mixture containing carbon dioxide, at least one gas of lower boiling point than carbon dioxide, and at least one gaseous impurity having a higher boiling point than carbon dioxide wherein pure gaseous carbon dioxide and a gas mixture having a reduced concentration of carbon dioxide and no gaseous impurity are produced.

SUMMARY OF THE INVENTION

According to the present invention, there is provided a method of purifying a gas mixture comprising carbon dioxide and at least one gaseous impurity of higher boiling point than carbon dioxide, and at least one gas of lower boiling point than carbon dioxide, comprising the steps of precooling the gas mixture to the dewpoint of the carbon dioxide or below, and then rectifying the gas mixture so as to form a liquid fraction relatively rich in the impurity or impurities and a product gaseous fraction relatively lean in or free from the gaseous impurity or impurities.

For complete removal of the impurity or impurities, the gas mixture to be purified should contain carbon dioxide at a high partial pressure of carbon dioxide. As an example FIG. 3 of the accompanying drawings (which is described in more detail below) shows the carbon dioxide content of the feed gas as a function of the total operating pressure. The partial pressure actually required for the complete removal of hydrogen sulphide impurity is given by the product of the percentage by volume of carbon dioxide in the feed gas mixture and the chosen total operating pressure.

The gaseous impurity or impurities may typically comprise one or more of the following compounds: hydrogen sulphide, carbon oxysulphide, mercaptans, hydrogen cyanide, and hydrocarbons having at atmospheric pressure a higher boiling point than carbon dioxide.

The gas or gases of lower boiling point may typically be one or more of the following gases: hydrogen, carbon monoxide, methane and nitrogen.

The method according to the invention makes possible complete selective separation of the gaseous impurity or impurities from the gas mixture and partial removal of carbon dioxide therefrom. The elimination of a need for the circulation and regeneration of a liquid solvent or absorbent considerably simplifies purification of the gas mixture and eliminates the risk of such liquid corroding the plant. At high initial partial pressures the carbon dioxide can provide sufficient refrigeration to avoid the use of an external source of refrigeration. Moreover, with the elimination of the need to perform a solvent or absorbent regeneration step, there is no need for an external heat supply, for example, in the form of steam.

BRIEF DESCRIPTION OF THE DRAWINGS

The method according to the present invention will now be described by way of example with reference to the accompanying drawings, of which.

DESCRIPTION OF PREFERRED
EMBODIMENTS OF THE INVENTION

Figure 1:
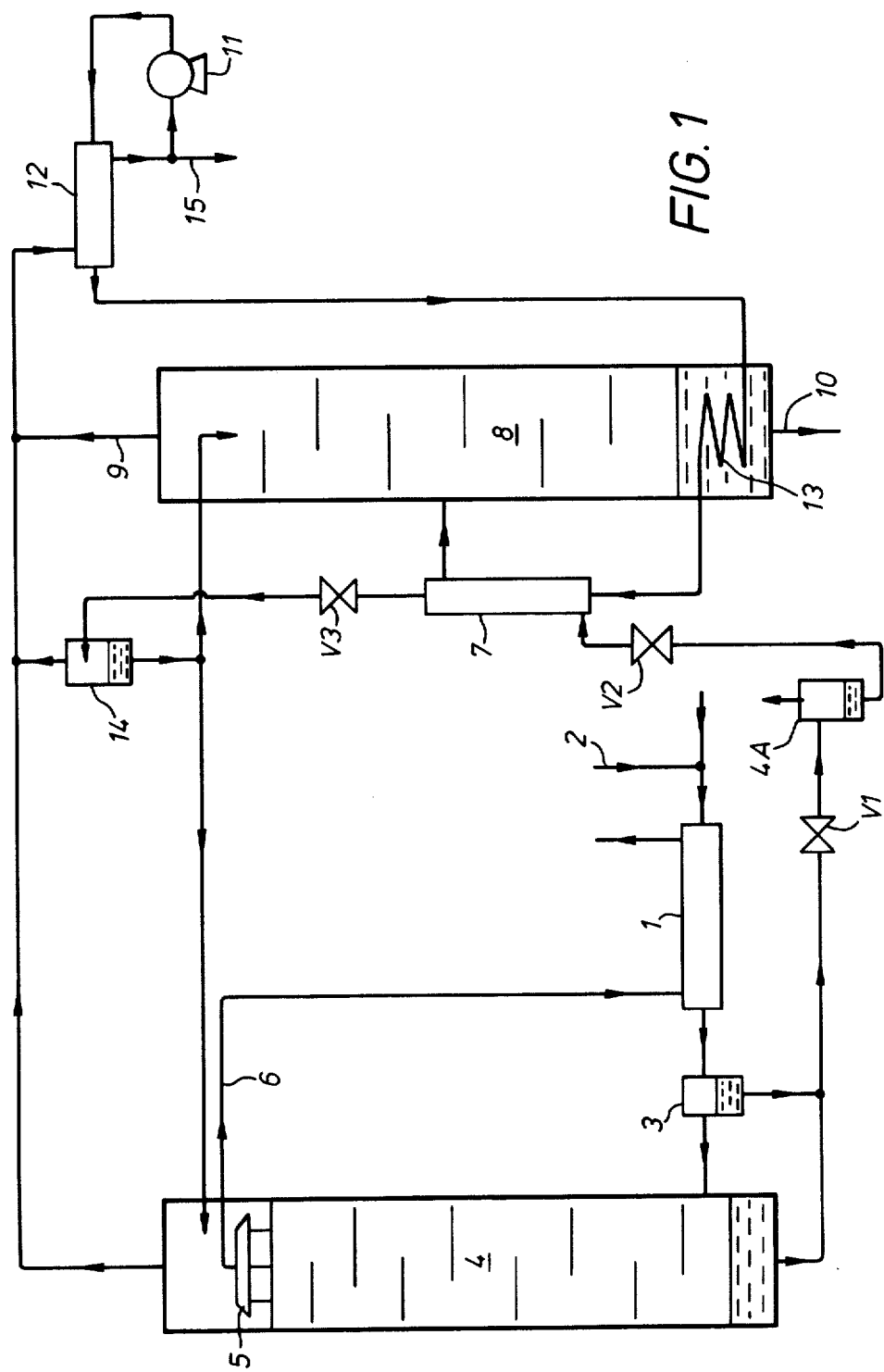
FIG. 1 is a schematic flow diagram illustrating one plant for performing the method according to the invention.

Referring to FIG. 1, a feed gas mixture rich in carbon dioxide and containing one or more gaseous impurities and one or more low boiling point gases enters a heat exchanger 1 at a temperature near to but above 273 K. and at a high pressure, normally above 40 atmospheres. Unless the feed gas mixture is dry a depressant of the freezing point of water (for example ethylene glycol) is added through a pipeline 2 to the feed gas mixture upstream of the heat exchanger 1 so as to prevent freezing of water in the heat exchanger 1. The feed gas mixture is cooled in the heat exchanger 1 to the dewpoint of the carbon dioxide or below. A separator 3 collects condensate that is typically formed. The condensate may, for example, comprise water, any heavy hydrocarbon impurities present in the feed gas mixture, some of the carbon dioxide and the corresponding quantity of gaseous impurities of sulphur that accords with the equilibrium between the gaseous impurities of sulphur and the carbon dioxide. In addition, some hydrogen, in particular, dissolves in the condensate. The condensate can be processed separately from the rest of the gas mixture or with another part of the gas mixture as shall be described below.

The uncondensed portion of the gas mixture is then passed into a rectification column 4 fitted with a condenser 5. A liquid fraction comprising substantially all the gaseous impurities in the gaseous mixture entering the rectification column 4 and about 63% of the carbon dioxide collects in the sump of the rectification column 4, leaving a gaseous fraction substantially free of the gaseous impurities and containing the remaining carbon dioxide. After rectification, the gaseous fraction enters the condenser 5 at the top of the column 4 and provides a condensate of liquid carbon dioxide, substantially free of gaseous impurities of higher boiling point than carbon dioxide, which is used as a reflux in the column 4. The uncondensed gas contains in addition to remaining carbon dioxide the non-condensible lower boiling point constituents. It passes out of the condenser 5 and enters a pipeline 6 which conducts it to the heat exchanger 1 through which it passes countercurrently to the incoming feed gas mixture providing the necessary cooling. It leaves the plant at practically the initial pressure of the feed gas mixture and with a small temperature difference. If desired, the remainder of the carbon dioxide can then be removed by a conventional purification plant. Since the bulk (typically 63% by volume) of the incoming carbon dioxide is removed by the method according to the invention the conventional purification plant can be much smaller than it would otherwise have to be.

The liquid collecting in the sump of the rectification column 4 is passed out of the column 4 and, if desired, combined with the condensate from the separator 3. The liquid is then subjected to further treatment for the selective separation of the impurities from the carbon dioxide by rectification. The nature of the treatment depends on whether it is desired to produce carbon dioxide substantially free of solutes, particularly dissolved hydrogen, or whether such gas can be tolerated mixed with the carbon dioxide. The plant illustrated in FIG. 1 is adapted to produce substantially pure carbon dioxide. For the production of substantially pure carbon dioxide the bulk of the solutes can be removed as flash gas by partial expansion through expansion valve V1 into a separator 4A. The flash gas can, if desired, by recompressed and recycled to the feed gas mixture upstream of the heat exchanger 1. The liquid collected in the separator is then expanded by being passed through an expansion valve V2 and is then vaporised in a second heat exchanger 7. The so-formed vapour is then introduced into the middle of a second rectification column 8 which operates at a pressure slightly above the triple point pressure (5.11 atmospheres) of carbon dioxide. If total removal of solutes is required a modified plant as described below with reference to FIG. 2 may be used.

The rectification column 8 produces a gaseous carbon dioxide fraction, practically free of impurities.

In addition, a liquid "tail" fraction, rich in impurities, is produced and is withdrawn from the bottom of the column 8 as through pipeline 10. It typically contains compounds of sulphur (generally mainly hydrogen sulphide) at a purity of up to 50% by volume. The liquid tail fraction is thus suitable for conversion to sulphur by the Claus process. It can be vaporised in the heat exchanger 1 or a third heat exchanger 12 (to be described below) thereby providing additional cooling.

Reflux and reboil are effected by a heat pump which uses the purified carbon dioxide as a working fluid. The cycle performed by the heat pump on the working fluid involves passing it through a compressor 11, a third heat exchanger 12 and a reboiler 13, the reboiler 13 being immersed in the liquid fraction produced at the bottom of the column 8.

Substantially pure carbon dioxide is withdrawn from the top of the rectification column 8 via pipeline 9 and is passed into the heat exchanger 12 where it is warmed. The carbon dioxide is then compressed in the compressor 11 and returned through the heat exchanger 12. After leaving the heat exchanger 12, the carbon dioxide then passes through the reboiler 13 causing some of the liquid fraction in the column 8 to be reboiled. After leaving the reboiler 13 the recycling carbon dioxide is then used in the heat exchanger 7 to effect vaporisation of the liquid passing through that heat exchanger from the expansion valve V2. The carbon dioxide (now liquid) is then expanded through an expansion valve V3 into a separator 14. The expansion produces a small amount of flash gas (carbon dioxide together with the remainder of any gaseous constituents of low boiling point which have not been removed in the separator 4A) which is separated from the remaining liquid (substantially pure carbon dioxide). Part of the liquid collected in the separator 14 is used as the coolant for the condenser 5 with the remainder being returned to the column 8 to serve as reflux. The temperature and pressure of the liquid carbon dioxide leaving the separator 14 are kept higher than at the triple point of carbon dioxide (216.6 K. and 5.11 atmospheres).

The flash gas from the separator 8 is united with vaporised carbon dioxide leaving the condenser 5 and with the gas in the pipeline 9 upstream of the heat exchanger 12, thus completing the cycle of operations performed on the working fluid by the heat pump.

A substantially pure gaseous carbon dioxide product is withdrawn from the circulating carbon dioxide immediately upstream of the compressor 11 at a pressure of about 5 atmospheres and at near ambient temperature. It can be expanded in a turbine (not shown) with performance of work, and the refrigeration thus obtained can be used to provide additional cooling where required.

Figure 3:
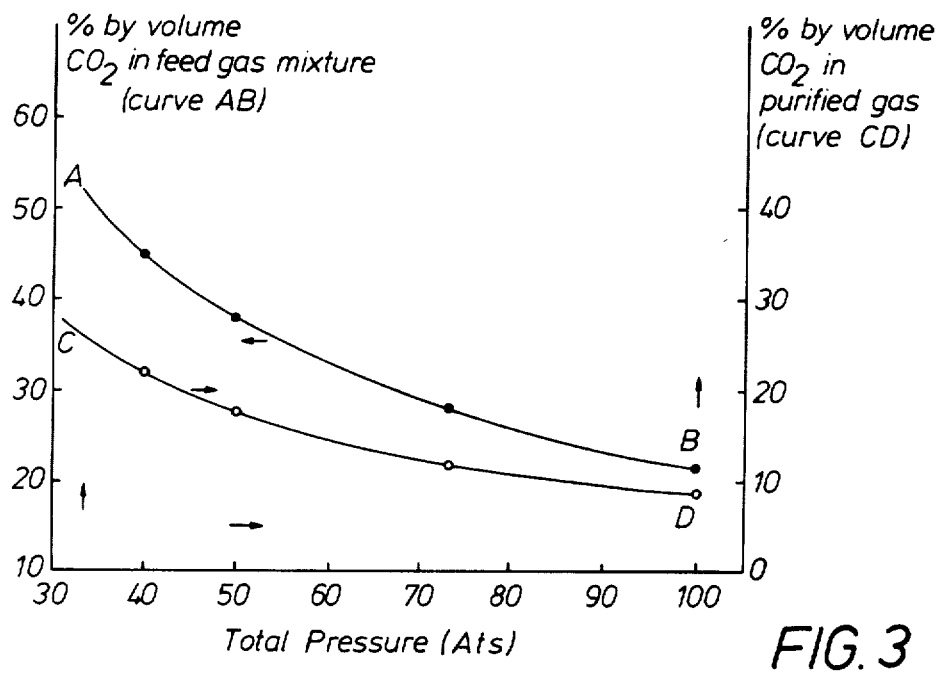
FIG. 3 shows graphically the carbon dioxide content of the feed gas required and the carbon dioxide content of the purified gas achievable for complete removal of hydrogen sulphide as a function of the total operating pressure.

FIG. 3 shows the carbon dioxide content of the feed gas required and the carbon dioxide content of the purified gas achievable for the complete removal of hydrogen sulphide as a function of the total operating pressure. Under these conditions adequate reflux in the column 4 is provided and 63% of the carbon dioxide in the feed gas mixture are recovered. The carbon dioxide content of the purified gas is then determined by the total gas pressure. To ensure that there is an adequate reflux ratio in the column 4 without having to rely on an external source of reflux a high partial pressure of carbon dioxide is required in the feed gas mixture. As can be seen from FIG. 3 the carbon dioxide partial pressure in the incoming gas mixture is generally about 20 atmospheres. This condition is, for example, met when gasifying heavy fuel oil by partial oxidation with oxygen and converting the carbon monoxide produced into hydrogen and carbon dioxide by reaction with steam.

If, for example, the feed gas mixture is at a pressure of 73 atmospheres and contains 27% by volume of carbon dioxide, and 1% by volume of hydrogen sulphide, the purified gas in the pipeline 6 will contain about 12% by volume of carbon dioxide (as shown in FIG. 3) and substantially no hydrogen sulphide.

There is as mentioned above no need for external refrigeration since cold losses by heat exchange or heat influx are substantially covered by the Joule-Thomson effect of the carbon dioxide expanding from its initial to its final partial pressure. As a further advantage the power consumption of the plant is therefore essentially that of the compressor 11 less the power recoverable by a turbine from the pure carbon dioxide unless the carbon dioxide is required at a pressure of about 5 atmospheres. If, as aforementioned, the flash gas from the separator 4A is recompressed before being recombined with the feed gas mixture, there will be a small additional power consumption. Even taking such additional power consumption into account, and also allowing for the removal of the remaining carbon dioxide from the purified gas in pipeline 6 by means of a conventional purification process, the total power consumption is low in comparison with previously known purification processes.

Figure 2:
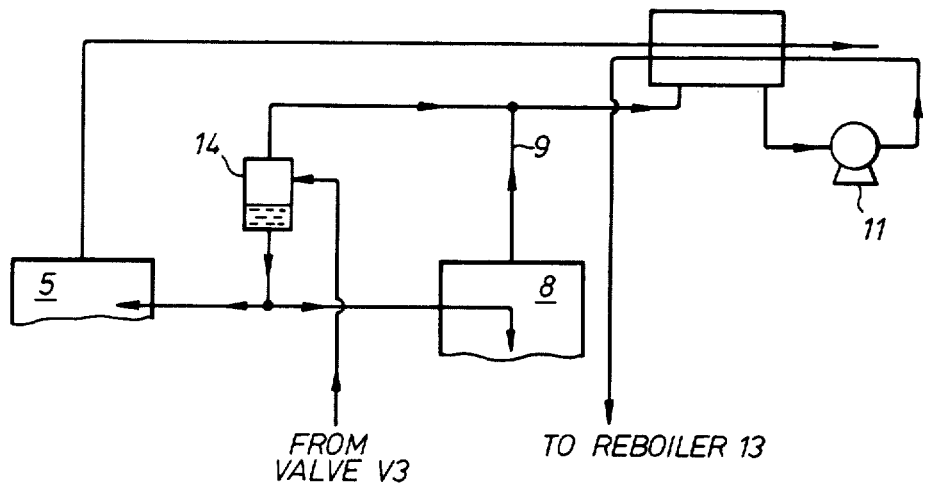
FIG. 2 is a schematic flow diagram illustrating part of another plant for performing the method according to the invention.

A modification to the plant illustrated in FIG. 1 is shown in FIG. 2. In this modification the evaporated carbon dioxide leaving the condenser 5 is not united with the flash gas from the separator 14 and the carbon dioxide in the pipeline 9. Instead, it is passed separately through the heat exchanger 12 and at least some of it (generally most) is then taken as product carbon dioxide. No product carbon dioxide is taken from immediately upstream of the compressor 11 in FIG. 2. The advantage of this modification is that it makes possible to produce a carbon dioxide product containing practically no constituents of lower boiling point than carbon dioxide.

The foregoing and other various changes in form and details may be made without departing from the spirit and scope of the present invention. Consequently, it is intended that the appended claims be interpreted as including all such changes and modifications.

I claim:

1. A method of purifying a gas mixture comprising between 10 to 60% carbon dioxide and at least one gaseous impurity of higher boiling point than carbon dioxide and at least one gas of lower boiling point than carbon dioxide, comprising the steps:
  (a) precooling the gas mixture to the dew point of the carbon dioxide or below;
  (b) rectifying the gas mixture in a first rectification column having a condenser and forming a liquid fraction relatively rich in the impurity or impurities and an uncondensed product gaseous fraction relatively lean in or free from the gaseous impurity or impurities, but containing a lower proportion of carbon dioxide than the gas mixture entering the first rectification column;
  (c) cooling the condenser with liquid carbon dioxide at a pressure and temperature above the pressure and temperature of carbon dioxide at its triple point, whereby a majority of the carbon dioxide in the gas mixture is condensed and serves as reflux in the first rectification column;
  (d) employing the uncondensed product gaseous fraction to precool the gas mixture in the said step (c);
  (e) withdrawing the liquid fraction from the first rectification column; expanding the liquid fraction, and vaporising it;
  (f) rectifying the vaporised liquid fraction in a second rectification column at a pressure and temperature higher than the pressure at the triple point of carbon dioxide and producing gaseous carbon dioxide substantially free of gaseous impurity and a tail liquid relatively rich in the gaseous impurity or impurities.

2. A method according to claim 1, in which after being withdrawn from the first rectification column but before being subjected to said expansion the liquid fraction is partially expanded to form a flash gas which is then separated from the remaining liquid.

3. A method according to claim 1, in which reflux and reboil for the second rectification column are provided by a heat pump in which carbon dioxide is the working fluid.

4. A method according to claim 3, in which the heat pump operates a cycle comprising the steps of warming the carbon dioxide in a heat exchanger; compressing the warmed carbon dioxide; cooling the carbon dioxide after compression in the said heat exchange; passing the cooled carbon dioxide through a reboiler in the second rectification column; subsequently liquefying the carbon dioxide by heat exchange with expanded liquid fraction from the first rectification column; expanding the liquefied carbon to produce a flash gas and a residual liquid; and passing one part of the residual liquid to the second rectification column and another part to the said condenser of the first rectification column.

5. A method as claimed in claim 1, in which the impurity or impurities are selected from the group of sulphur compounds comprising hydrogen sulphide, carbon oxysulphide and mercaptans.

6. A method of purifying a gas mixture comprising between 10–60% carbon dioxide and at least one gaseous impurity of higher boiling point than carbon dioxide and at least one gas of lower boiling point than carbon dioxide, comprising the steps of:
(a) precooling the gas mixture to the dewpoint of the carbon dioxide or below in a first heat exchanger;
(b) rectifying the gas mixture in a first rectification column having a condenser and forming a liquid fraction relatively rich in the impurity or impurities and an uncondensed product gaseous fraction relatively lean in or free from the gas impurity or impurities, but containing a lower concentration of carbon dioxide than the gas mixture entering the first rectification column;
(c) cooling the condenser with liquid carbon dioxide at a pressure and temperature above the pressure and temperature of carbon dioxide at its triple point, whereby a majority of the carbon dioxide in the gas mixture is condensed and serves as reflux in the first rectification column;
(d) employing the uncondensed product gaseous fraction to precool the gas mixture in the said step (a);
(e) withdrawing the liquid fraction from the first rectification column, expanding the liquid fraction and then vaporising it in a second heat exchanger;
(f) rectifying the vaporised liquid fraction in a second rectification column at a pressure and temperature higher than the pressure at the triple point of carbon dioxide and producing gaseous carbon dioxide substantially free of gaseous impurity and a tail liquid relatively rich in the gaseous impurity or impurities;
(g) providing reflux and reboil for the second rectification column by:
  (i) withdrawing gaseous carbon dioxide from the top of the second rectification column;
  (ii) warming the carbon dioxide in a third heat exchanger;
  (iii) compressing the warmed carbon dioxide;
  (iv) cooling the carbon dioxide after compression in the third heat exchanger;
  (v) passing the cooled carbon dioxide through a reboiler in the second rectification column;
  (vi) subsequently liquefying the carbon dioxide in the second heat exchanger;
  (vii) expanding the so-formed liquid carbon dioxide to form a flash gas and a residual liquid;
  (viii) passing a part of the residual liquid to the second rectification column to act as reflux, and another part of the residual liquid to cool the condenser in the first rectification column; and
  (ix) recombining the flash gas with the gaseous carbon dioxide withdrawn from the second rectification column.

7. A method according to claim 6, in which gaseous carbon dioxide is withdrawn as product and expanded in a turbine with performance of work and creation of refrigeration.

8. A method according to claim 6, in which vaporised carbon dioxide is withdrawn from the second condenser and is passed through the third heat exchanger separately to the flash gas produced by expanding the said so-formed liquid carbon dioxide, and to the gaseous carbon dioxide withdrawn from the second rectification column, and taking at least some of the said vaporised carbon dioxide as a product after passage through the third heat exchanger.

9. A method according to claim 6, in which the impurity or impurities are selected from the group comprising hydrogen sulphide, carbon oxysulphide and mercaptans, the gas mixture includes hydrogen, and the liquid fraction withdrawn from the first rectification column is twice expanded before being vaporised, the first expansion producing a flash gas comprising hydrogen.

10. A method according to claim 6, in which the partial pressure of the carbon dioxide in the gas mixture before precooling is about 20 atmospheres.

* * * * *